(12) United States Patent
Monteilliet et al.

(10) Patent No.: US 9,052,233 B2
(45) Date of Patent: Jun. 9, 2015

(54) SENSOR FOR VENOUS NETWORKS OF A PART OF A LIVING BODY

(75) Inventors: Gilles Monteilliet, Issy-les-Moulineaux (FR); Matthieu Darbois, Issy-les-Moulineaux (FR); Sylvaine Picard, Issy-les-Moulineaux (FR); Michel Cruchaga, Issy-les-Moulineaux (FR)

(73) Assignee: MORPHO, Issy-les-Moulineaux (FR)

( * ) Notice: Subject to any disclaimer, the term of this patent is extended or adjusted under 35 U.S.C. 154(b) by 114 days.

(21) Appl. No.: 14/001,003

(22) PCT Filed: Feb. 22, 2012

(86) PCT No.: PCT/EP2012/053021
§ 371 (c)(1),
(2), (4) Date: Dec. 3, 2013

(87) PCT Pub. No.: WO2012/126691
PCT Pub. Date: Sep. 27, 2012

(65) Prior Publication Data
US 2014/0077082 A1   Mar. 20, 2014

(30) Foreign Application Priority Data
Mar. 18, 2011   (FR) ...................................... 11 52263

(51) Int. Cl.
| *G01J 1/04* | (2006.01) |
| *A61B 5/117* | (2006.01) |
| *A61B 5/1455* | (2006.01) |
| *A61B 5/00* | (2006.01) |
| *G06K 9/00* | (2006.01) |
| *G06K 9/20* | (2006.01) |

(52) U.S. Cl.
CPC ............... *G01J 1/0407* (2013.01); *A61B 5/117* (2013.01); *A61B 5/1455* (2013.01); *A61B 5/489* (2013.01); *G06K 9/00013* (2013.01); *G06K 2009/00932* (2013.01); *G06K 9/2027* (2013.01)

(58) Field of Classification Search
CPC ....................................................... G01J 1/0407
USPC ........................................ 250/340, 353, 338.1
See application file for complete search history.

(56) References Cited

U.S. PATENT DOCUMENTS

| 2005/0047632 A1 | 3/2005 | Miura et al. |
| 2008/0063243 A1 | 3/2008 | Kiyomizu et al. |
| 2010/0092047 A1 | 4/2010 | Yamamoto et al. |

FOREIGN PATENT DOCUMENTS

| EP | 2 241 998 | 10/2010 | |
| JP | 2004234178 A | * 8/2004 | ................ G06T 1/00 |
| JP | 2008/54787 | 3/2008 | |

OTHER PUBLICATIONS

English-language translation of Written Opinion of the International Searching Authority for International Application No. PCT/EP2012/053021 mailed Oct. 19, 2013.
International Search Report for PCT/EP2012/053021 mailed May 22, 2012.
Written Opinion of the International Searching Authority mailed May 22, 2012.

* cited by examiner

*Primary Examiner* — David Porta
*Assistant Examiner* — Faye Boosalis
(74) *Attorney, Agent, or Firm* — Nixon & Vanderhye, PC

(57) ABSTRACT

A sensor for venous networks of a part of a living body, having
  an infrared illumination source,
  a waveguide illuminated by the infrared illumination source and having, on one face, at least one extraction zone intended to extract the infrared rays from the waveguide in at least one main extraction direction,
  an image acquisition means disposed opposite the one face so as to define between them a passage through the entrance of which the part of the living body can enter, and having a sensitive element,
  the or each extraction zone being such that the or each main extraction direction of the extraction zone oriented so as not to intercept the sensitive element.

18 Claims, 5 Drawing Sheets

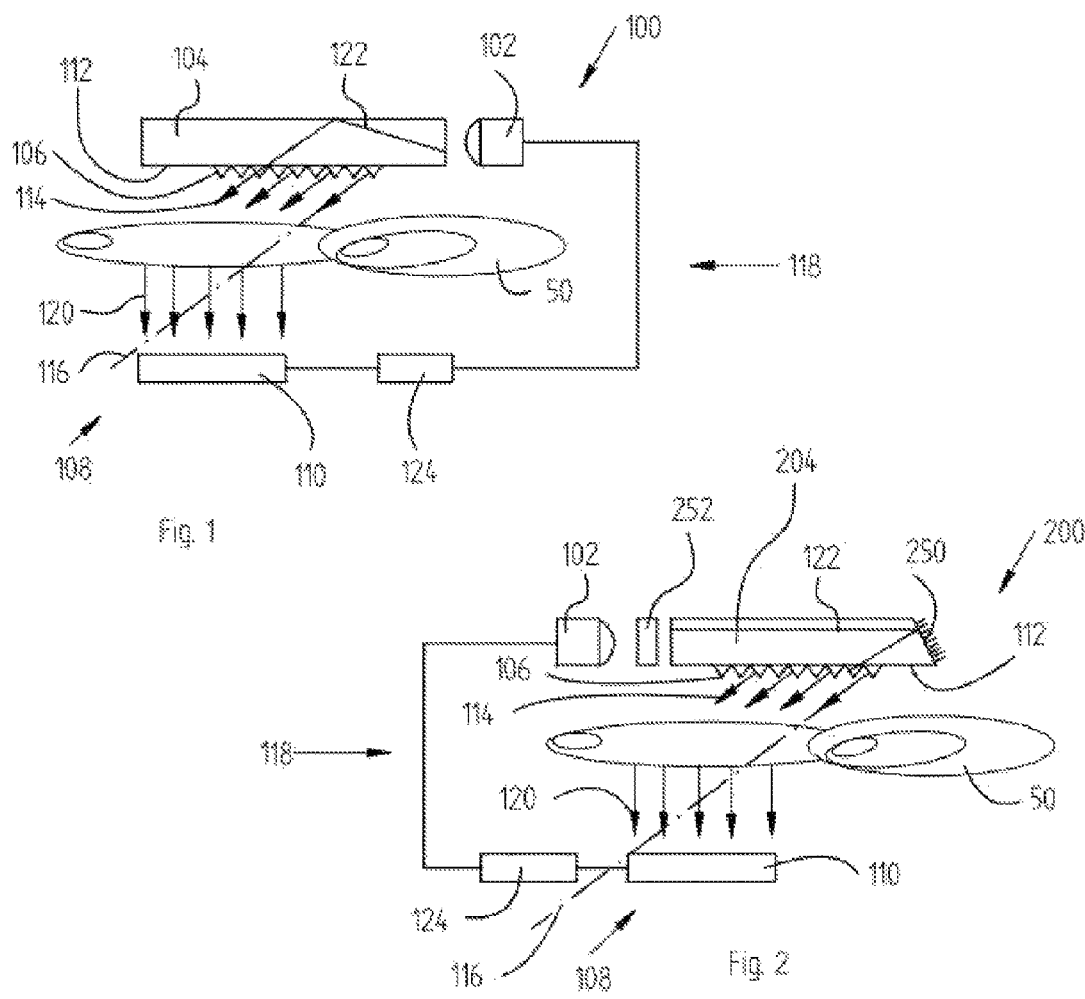
Fig. 1
Fig. 2
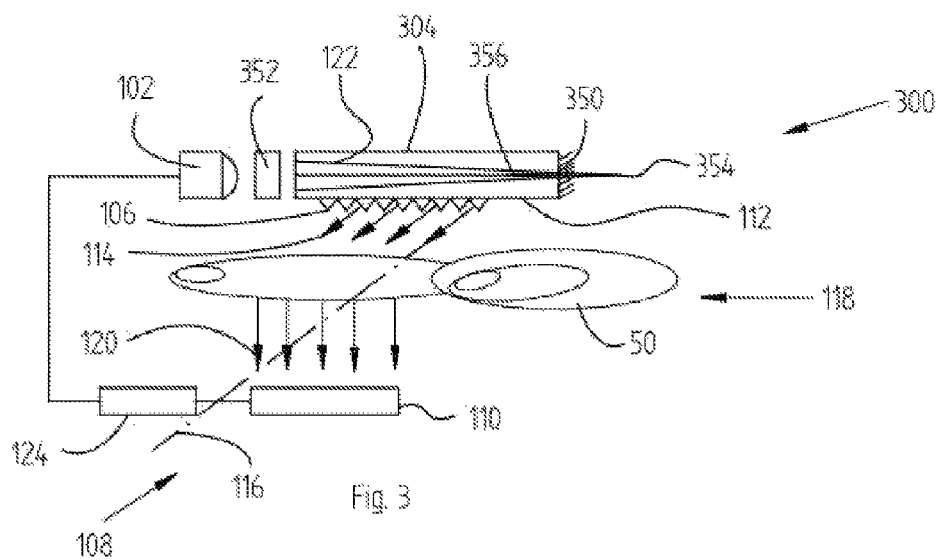
Fig. 3

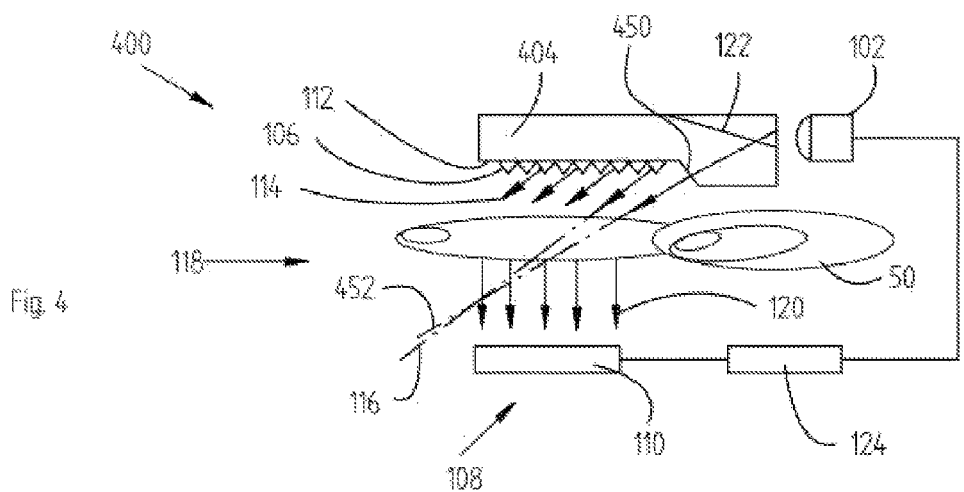
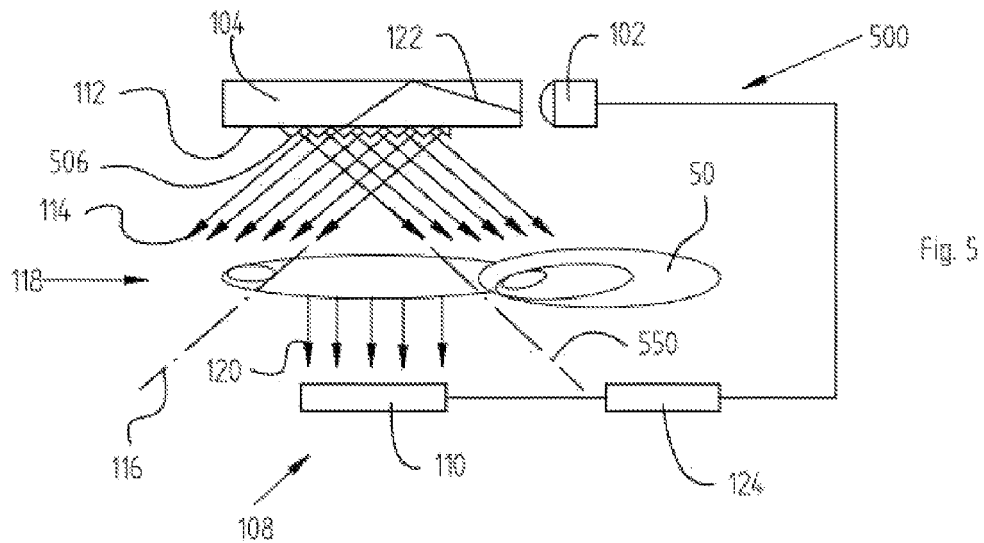
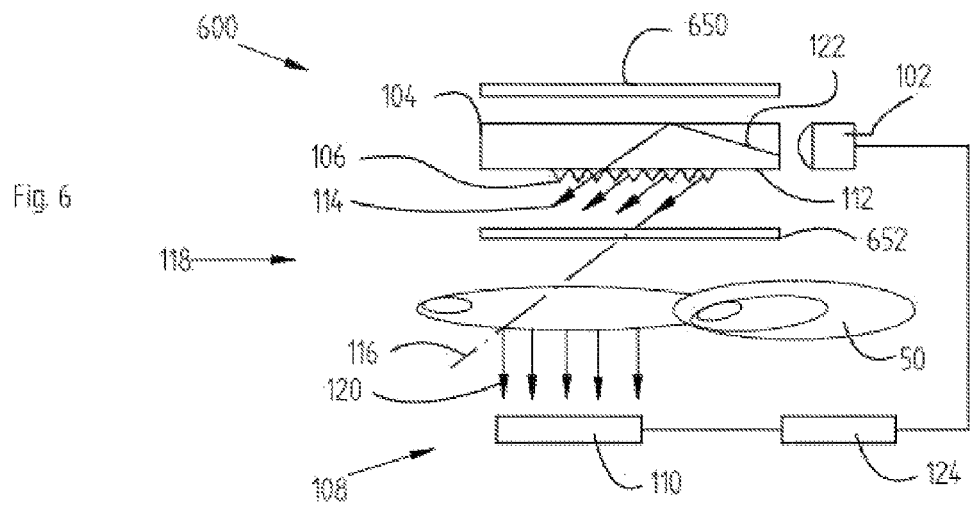

SENSOR FOR VENOUS NETWORKS OF A PART OF A LIVING BODY

This application is the U.S. national phase of International Application No. PCT/EP2012/053021 filed 22 Feb. 2012 which designated the U.S. and claims priority to FR 11/52263 filed 18 Mar. 2011, the entire contents of each of which are hereby incorporated by reference.

BACKGROUND OF THE INVENTION

1. Field of the Invention

The present invention concerns a sensor for venous networks of a part of the living body, as well as a method for controlling such a sensor.

2. Description of Related Art

A sensor for venous networks of a part of a living body such as that of a finger, a hand, a toe, etc. is very much used, for example for controlling access to a site or a machine.

A venous network sensor comprises an infrared illumination source that illuminates a means for acquiring images from the sensor, such as for example a CCD camera.

This infrared illumination source is implemented by a set of infrared emitters that are normally positioned with respect to one another along rows and/or columns. Arrays or matrices of infrared emitters are then spoken of.

When a living body is placed between the infrared illumination source and the image acquisition means, some rays in the flow of light strike the image acquisition means directly and others strike this image acquisition means after having passed through the living body. The image thus acquired is then processed digitally so that the venous network of the living body appears on this image. A user can then be authenticated by comparing the venous network thus acquired and the venous network that he previously recorded.

Though the principle of a venous network sensor is simple, the use thereof may pose the problem of overexposure of the acquired image. This is because the rays that strike the image acquisition means directly cause an intensity of the pixels of the image that is great compared with that caused by the rays that pass through the living body. This difference in intensity causes artefacts on the acquired image, such as a light halo or local overintensities, especially at the edges of the living body. This is particularly true for systems capturing on the fly since the position of the object to be acquired may be constrained. These artefacts interfere with the processing operations that are applied to the acquired image in order to reveal the venous network.

To improve the quality of acquisition of the venous network, various solutions have been proposed. For example, a venous network sensor is known in which the activation of the infrared emitters is linked to the detection of the presence of a living body.

Such a venous network sensor does not give entire satisfaction.

The documents US-A-2005/047632, US-A-2008/06243 and US-A-2010/092047 disclose venous network sensors.

BRIEF SUMMARY OF THE INVENTION

One object of the present invention is to propose a sensor for venous networks of a part of a living body that does not have the drawbacks of the prior art and in particular avoids saturating the image acquisition means whether the living body be present or absent.

To this end, a sensor for venous networks of a part of a living body is proposed, comprising:
 an infrared illumination source, and
 an image acquisition means,
 said sensor being characterised in that it furthermore comprises a waveguide illuminated by said infrared illumination source and having at least one extraction zone intended to extract the infrared rays from said waveguide through an extraction face of the waveguide in at least one main extraction direction,
 in that said image acquisition means is disposed facing said extraction face so as to define between them a passage through the entrance of which said part of the living body can enter, and comprising a sensitive element, and
 in that the or each extraction zone is such that the or each main extraction direction is oriented so as not to intercept said sensitive element.

According to a particular embodiment, said or each extraction zone is carried by the face opposite to the extraction face.

According to another particular embodiment, said or each extraction zone is carried by the extraction face.

Advantageously, said or at least one of said extraction zones consists of an inclined facet produced in said extraction face.

Advantageously, said or at least one of said extraction zones consists of microprisms.

Advantageously, the inclined facet is upstream of the microprisms in the direction of progression of the infrared rays in the waveguide.

According to a particular embodiment, the light source is disposed opposite the entrance of the passage, the sensor comprises a collimation means disposed between the illumination source and the waveguide and designed to collimate close to infinity the infrared rays issuing from the illumination source, and the waveguide has, on the path of the infrared rays thus collimated, a reflective surface having an angle of inclination designed to bend the infrared rays transmitted and divert them to the or each extraction zone.

According to another particular embodiment, the light source is disposed opposite the entrance of the passage, the sensor comprises a focusing means disposed between the illumination source and the waveguide and designed to focus the infrared rays issuing from the illumination source towards a focusing point, and the waveguide has, on the path of the infrared rays thus focused, a reflective surface disposed at a distance from the focusing point and designed to reflect the infrared rays and cause diversion thereof towards the extraction zone.

According to another particular embodiment, said waveguide has a first extraction zone and a second extraction zone, said infrared illumination source has a first illuminating element illuminating the edge of the waveguide disposed on the passage entrance side and a second illuminating element illuminating the edge of the waveguide disposed on the side opposite to the passage entrance, the first extraction zone is disposed between the first illuminating element and the second extraction zone and is designed to extract the infrared rays issuing from the first illuminating element, the second extraction zone is disposed between the second illuminating element and the first extraction zone and is designed to extract the infrared rays issuing from the second illuminating element, and the extraction zones are such that the infrared rays extracted by the first extraction zone and the infrared rays extracted by the second extraction zone converge towards each other at the point in the passage where the part is liable to be positioned.

Advantageously, the sensor comprises a protective plate placed opposite the face opposite to the extraction face and consisting of a material preventing the passage of the infrared rays but allowing the rays in the visible spectrum to pass.

Advantageously, the sensor comprises a filtering plate placed between the extraction zone and the passage and consisting of a material preventing the passage of the rays in the visible spectrum but allowing the infrared rays to pass.

Advantageously, the sensor comprises control means designed to control the illumination source for power.

Advantageously, the control means consist of a control unit provided for controlling the illumination source and at least one detection means provided for sending, to said control unit, a value representing the illumination power that it receives, the control unit comprising means for controlling the illumination source according to said value.

According to a particular embodiment, the or each detection means is placed in the vicinity of the sensitive element.

According to another particular embodiment, the or each detection means is disposed in the vicinity of the extraction zone or zones.

Advantageously, the or each detection means is disposed at the bottom of a hole produced in the waveguide, each of said holes having an axis substantially parallel to the extraction direction.

Advantageously, the surface of the or each hole is covered with a material impermeable to infrared rays.

The invention also proposes a method for controlling a sensor according to some of the above variants, said method comprising:
- an initialisation step, during which the detection means sends to the control unit the reference value representing the light power that it receives in the absence of the part,
- a sending step during which the detection means sends to the control unit a value representing the light power that it receives,
- a calculation step during which the control unit calculates the difference between the value thus received and the reference value,
- a test step, during which the control unit checks whether the difference thus calculated is greater, in absolute value, than a predetermined difference,
- if the difference thus calculated remains less than the predetermined difference, a looping step during which the process loops back onto the sending step,
- if the difference thus calculated is greater than the predetermined difference, a control step during which the control unit demands an increase in the light power emitted by the illumination source, and
- a return step during which the process loops back onto the sending step.

BRIEF DESCRIPTION OF THE DRAWINGS

The features of the invention mentioned above, as well as others, will emerge more clearly from a reading of the following description of an example embodiment, said description being given in relation to the accompanying drawings, among which:

FIG. 1 shows a side view of a venous network sensor according to a first embodiment of the invention, FIG. 2 shows a side view of a venous network sensor according to a second embodiment of the invention, FIG. 3 shows a side view of a venous network sensor according to a third embodiment of the invention, FIG. 4 shows a side view of a venous network sensor according to a fourth embodiment of the invention, FIG. 5 shows a side view of a venous network sensor according to a fifth embodiment of the invention, FIG. 6 shows a side view of a venous network sensor according to a sixth embodiment of the invention.

DETAILED DESCRIPTION OF THE INVENTION

Figure 7:
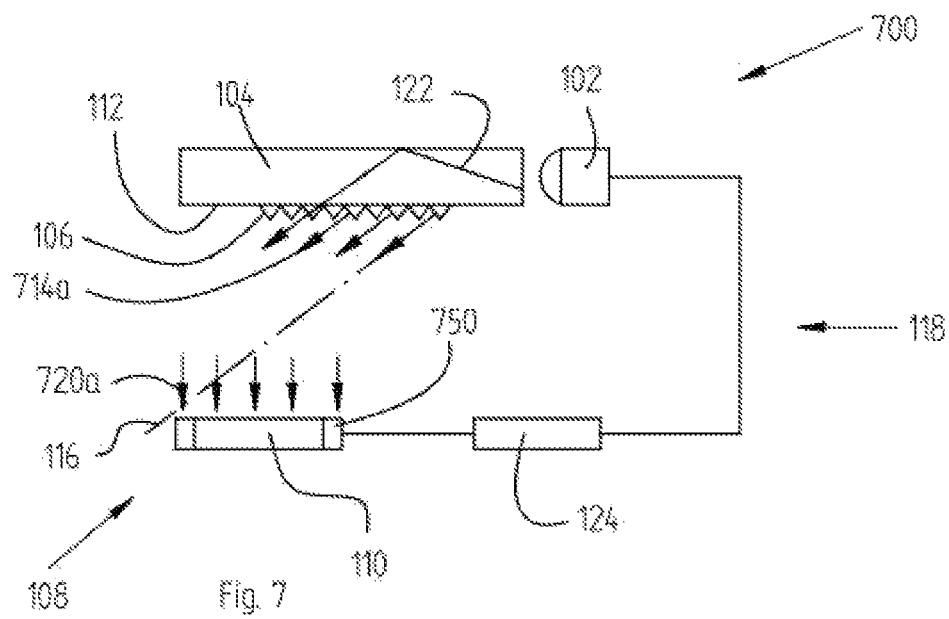
FIG. 7 shows a side view of a venous network sensor according to a seventh embodiment of the invention in the absence of the living body.

FIG. 1 shows a sensor 100 designed to capture, on the fly or statically, an image of the venous networks of a part 50, here a finger, of a living body.

The sensor 100 comprises:
- an infrared illumination source 102,
- a waveguide 104 illuminated by said infrared illumination source 102 and having on one face 112 at least one extraction zone 106 intended to extract the infrared rays 114 from said waveguide 104, in at least one main extraction direction 116,
- an image acquisition means 108 disposed opposite said face 112 so as to define between them a passage 118 through the entrance of which said part 50 of the living body can enter, and comprising a sensitive element 110, the or each extraction zone 106 being such that the or each main extraction direction 116 of said extraction zone 106 is oriented so as not to intercept said sensitive element 110.

The face 112 where the extraction zone 106 is disposed constitutes the extraction face 112 through which the infrared rays 114 are extracted.

The illumination source 102 is for example an array of diodes.

The waveguide 104 is for example a PMMA (polymethyl methacrylate) sheet the four edges of which have been polished and at least one of the edges of which is illuminated by the illumination source 102.

In the embodiment of the invention presented in FIG. 1, only one edge in thickness is illuminated and the face 112 that carries the extraction zone 106 is perpendicular to this edge.

In order to increase the reflections internal to the waveguide 104 and especially to minimise leakages of light to the outside, the other three edges are covered with successive layers of non-woven PVC adhesive (for example the adhesive from the TESA company bearing the reference: Tesa® Ruban PVC 4163) and aluminium adhesive (for example adhesive from the TESA company bearing the reference: Tesa® Ruban aluminium 50565).

The image acquisition means 108 is for example of the CCD camera type and comprises a sensitive element that may itself be divided into several sensitive sub-elements.

An element is sensitive in that it delivers information representing the light power that it receives. The information thus delivered is then transmitted to a control unit 124 that reconstructs an image of the venous network thus observed.

The image thus reconstructed can then be used in the context of an authentication procedure by comparing this image with reference images.

The control unit 124 also controls the switching on of the illumination source 102. The triggering of the switching-on command may be subject to the detection of the presence of the part of the body 50, for example the establishment of an infrared barrier. In another particular case, it is possible for the illumination source 102 to be permanently switched on.

The extraction zone 106 is here in the form of a patch that is optically coupled to the face 112 of the waveguide 104. That is to say the extraction zone 106 is on the extraction face 112.

The patch is intended to orient the extracted infrared rays 114 appropriately. The patch comprises here prisms, and it may for example be a polyester or polycarbonate film supporting a grooved surface structure in the form of microprisms with a symmetrical or asymmetrical profile, such as for example the film from the Luminit company bearing the reference DTF. The height of the symmetrical microprisms is for example around 100 μm. The angle of the microprisms is chosen so as to obtain the required angle for the extracted infrared rays 114.

In the embodiment presented here, the microprisms are pressed on the waveguide 104 through their bases, by means of an optical coupling means such as for example an index liquid or a transparent optical adhesive that improves the coupling between the two and enables the infrared rays 114 to be extracted to the outside of the waveguide 104.

Naturally it is possible to provide other means to enable infrared rays 114 to be extracted. In particular, it is possible to etch microprisms in the waveguide 104.

For each elementary extraction zone, that is to say here on each microprism, the profile of the luminance of the infrared rays issuing from this elementary extraction zone is in the form of a lobe the main extraction direction 116 of which constitutes the direction of maximum luminance.

The nominal flux is around 1 W, as for example in the case an image sensor 110 of the DALSA 4M60 type, with a passage 118 with a width of around 6 cm and a light source 102 consisting of diodes such as for example diodes from the OSRAM company bearing the reference SFH4235-EB.

Not all the light flux extracted from the waveguide 104 is sent to the sensitive element 110.

The infrared rays issuing from the illumination source 102 propagate in the waveguide 104 in the form of transmitted waves 122 and, after extraction from the waveguide 102, in the form of extracted infrared rays 114.

In the absence of the finger 50, the infrared rays 114 extracted by each microprism are sent on a main emission lobe that does not directly intercept the sensitive element 110, which avoids saturation thereof. When the finger 50 is present, the extracted infrared rays 114 are diffused in the finger 50 and absorbed by the haemoglobin before re-emerging in the form of emerging rays 120, which are intercepted by the sensitive element 110 but have a reduced light power that does not cause saturation thereof.

In the remainder of the description, various embodiments of the invention are described. For each of these embodiments, the elements common with the embodiment of the invention of FIG. 1 bear the same references.

FIG. 2 shows a second embodiment of the invention.

In an embodiment of the invention in FIG. 1, the illumination source 102 is disposed alongside the entrance of the passage 118. Such a location may cause heating of the sensor 100 at this entrance, with the risk of burning said part 50.

FIG. 2 shows a sensor 200 having a layout in which the light source 102 is opposite the entrance of the passage 118.

Since, in order to obtain the best results, the illumination must come from the back of the hand, it is necessary for the light rays 122 in the waveguide 204 to undergo bending.

The sensor 200 thus comprises a collimation means 252 disposed between the illumination source 102 and the waveguide 204 and is designed to collimate close to infinity the infrared rays issuing from the illumination source 102 and transmitted inside the waveguide 204.

The waveguide 204 has, on the path of the infrared rays 122 thus collimated in the waveguide 204, a reflective surface 250 having an angle of inclination designed to turn the transmitted infrared rays 122 in the waveguide 204 and divert them towards the extraction zone 106.

In the embodiment of the invention presented in FIG. 2, the reflective surface 250 is produced on the edge opposite to the edge illuminated by the light source 102.

FIG. 3 shows a sensor 300 also having a layout in which the light source 102 is opposite to the entrance of the passage 118.

The sensor 300 comprises a focusing means 352 disposed between the illumination source 102 and the waveguide 304 and is designed to focus the infrared rays issuing from the illumination source 102 and transmitted inside the waveguide 304 towards a focusing point 354.

The waveguide 304 has, on the path of the infrared rays 122 thus focused inside a waveguide 304, a reflective surface 350 that is disposed at a distance from the focusing point 354.

When the infrared rays 122 encounter the reflective surface 350, they are reflected towards a reflection point 356 that causes them to be turned in the waveguide 304 and diverts them towards the extraction zone 106.

In the embodiment of the invention presented in FIG. 3, the reflective surface 350 is produced on the edge opposite to the edge illuminated by the light source 102, and the focusing point 354 is situated beyond the reflective surface 350 in the direction of propagation of the infrared rays from the illumination source 102.

FIG. 4 shows a sensor 400 the extraction zone 450 of which is formed by an inclined surface that is here an inclined facet producing the face 112. The microprisms of the previous embodiments are therefore here replaced with the inclined facet 450 that makes it possible to extract the infrared rays 122 from the waveguide 404 in a main extraction direction 452 that does not intercept the sensitive element 110.

In the embodiment in FIG. 4, the illumination source 102 is on the same side as the passage entrance 118, but it is possible to combine the embodiments in FIGS. 2 and 3 in order to offset the illumination source 102 on the opposite side.

The main extraction direction 452 is merged with the normal to the inclined facet 450.

With the microprisms, a fraction of the infrared rays 114 does not escape in the main extraction direction 116. The surfaces of the microprisms are then luminous from the point of view of the sensitive element 110. Even if this is not a problem, some applications may require the reduction of this interference.

The establishment of the inclined facet 450, which constitutes a lenticular surface for controlling the luminous lobe of the infrared rays, reduces these phenomena.

It is also possible to combine the principle of an extraction zone 106 consisting of microprisms and an extraction zone 450 consisting of the inclined facet 450 to enable fine control of the illumination of the finger 50.

In this last embodiment, the inclined facet 450 is upstream of the microprisms in the direction of progression of the infrared rays 122 in the waveguide 404 to reinforce the illumination at the rear of the finger 50, which is the most relevant zone from the point of view of recognition by venous network.

FIG. 5 shows a sensor 500 similar to the one in FIG. 1 but in which the extraction zone 506 is such that it is designed to extract the infrared rays 114 from the waveguide 104 in a plurality of main extraction directions 116 and 550.

This embodiment makes it possible to illuminate a large volume.

In the embodiment in FIG. 5, there are two main extraction directions 116 and 550, which are substantially orthogonal to each other but which as before do not intercept the sensitive element 110.

The extraction zone 506 is here produced from microprisms with double emission lobes.

The extraction zone 506 consists for example of a film from the company Vikuiti 3M bearing the reference BEF.

In another embodiment, each microprism possesses two extraction slopes at 20° and the main extraction direction is then at 70° with respect to the extraction face 112 and the two emission lobes then have an angle of 40° with respect to each other.

Naturally it is possible to combine the embodiment in FIG. 5 with the embodiments in FIGS. 1 to 4.

FIG. 6 shows a sensor 600 that is similar to the one in FIG. 1.

To facilitate the positioning of his part of the body 50, the user must be able to see his body part 50 through the waveguide 104. For this purpose, he can place himself above the waveguide 104 and see through the top face, which is the face opposite to the face 112 carrying the extraction zone 106.

In order to limit the transmission of infrared rays towards the outside of a waveguide 104 through the top face, a protective plate 650 is disposed opposite said top face. This protective plate 650 consists of a material preventing the passage of infrared rays but allowing the rays in the visible spectrum to pass at least partially.

This protective plate 650 may for example be produced from an architectural glass from the company Schott DESAG bearing the reference IMERA D4218.

In the case of an authentication procedure, it is possible to combine the analysis of the venous network and the analysis of the fingerprint of the finger 50.

A supplementary device is then necessary. This supplementary device comprises a visible light source that illuminates the bottom face of the finger 50 and a suitable acquisition means that captures the image of the print of this finger 50 thus illuminated.

However, in the context of the capture of the image of the venous network, it is preferable to avoid the extraction zone 106 being illuminated by the light rays emitted by the visible-light source.

To this end, a filtering plate 652 is disposed between the extraction zone 106 and the passage 118, that is to say between the extraction zone 106 and the finger 50. This filtering plate 652 consists of a material preventing the passage of the rays in the visible spectrum but allowing infrared rays to pass. The finger 50 therefore passes between the filtering plate 652 and the sensitive element 110.

This filtering plate 652 may for example be produced from an architectural glass from the company Schott DESAG bearing the reference IMERA D4403.

Figure 8:
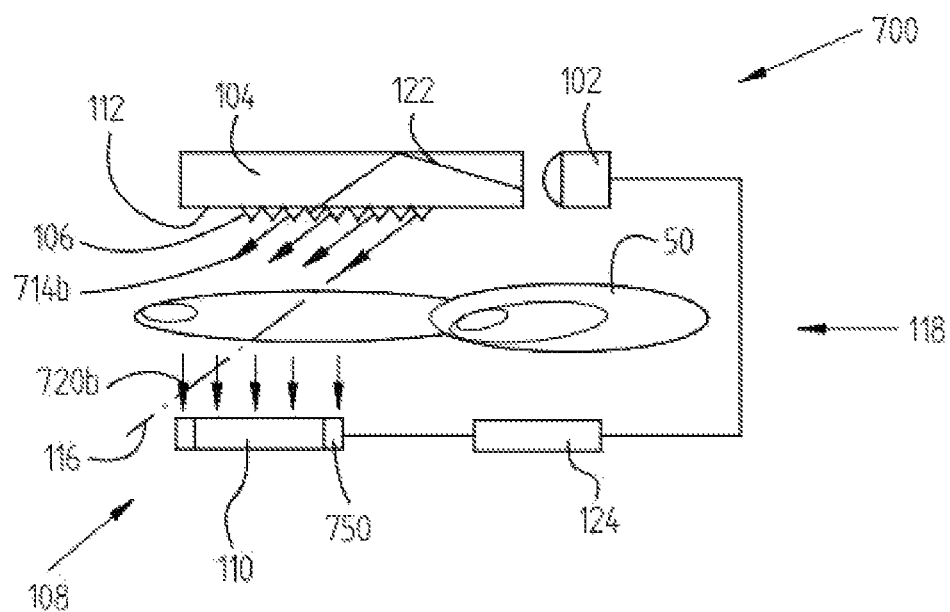
FIG. 8 shows a side view of a venous network sensor of FIG. 7 with the living body present.

FIG. 7 and FIG. 8 show a sensor 700 comprising means of controlling the illumination source 102 in order to control the illumination source 102 for power depending on whether the finger 50 is present or not in the passage 118. As for the other embodiments, this new embodiment is presented in the context of a sensor 700 similar to the one in FIG. 1, but it may apply to the embodiments in the other Figs.

In FIG. 7, the finger 50 is not present and in FIG. 8 the finger 50 is present.

The sensor 700 comprises, in the vicinity of the sensitive element 110, at least one detection means 750 that is for example of the photodetector type and is not intercepted by the infrared rays 714a, 714b extracted from the waveguide 104 in the main extraction direction 116.

The control means consist here of the detection means 750 and the control unit 124.

In the absence of the finger 50 and because of the diffusion of the infrared rays 714a emitted by the illumination source 102 and transmitted by the extraction zone 106, the detection means 750 receives a portion 720a of these infrared rays 714a.

During an initialisation step, the detection means 750 sends to the control unit 124 a reference value representing the light power that it receives in the absence of the finger 50.

During normal functioning, the detection means 750 regularly sends to the control unit 124 a value representing the light power that it receives.

If the newly received value does not deviate from the reference value by more than a predetermined difference, that is to say if the finger 50 is not present, nothing occurs.

If the newly received value deviates from the reference value by more than the predetermined difference, that is to say if the finger 50 is present and a drop in the light power received by the detection means 750 is observed, the control unit 124 controls the illumination source 102 so as to increase the light power emitted as long as the value sent by the detection means 750 remains distant from the reference value.

According to another embodiment of the invention, it is possible that the geometry of the sensor may be such that emission lobe is narrow and the detection means 750 receives no light flow in the absence of the finger 50. The positioning of the finger 50 will then give rise to an increase in the light power received by the detection means 750 and a reaction on the control unit 124 will control the illumination source 102 so as to reduce the light power emitted.

FIG. 8 shows the case where the finger 50 is present and the power emitted by the illumination source 102 has been increased. The infrared rays 714b transmitted through the extraction zone 106 then have a higher power while the power of the infrared rays 720b that have passed through the finger 50 has substantially the same light power as that of the infrared rays 720a corresponding to the case where the finger 50 is absent.

The control unit 124 comprises means for controlling the illumination source 102 according to the value that it receives from the detection means 750.

Thus the control takes account of the permeability of the finger 50 to infrared rays.

Figure 11:
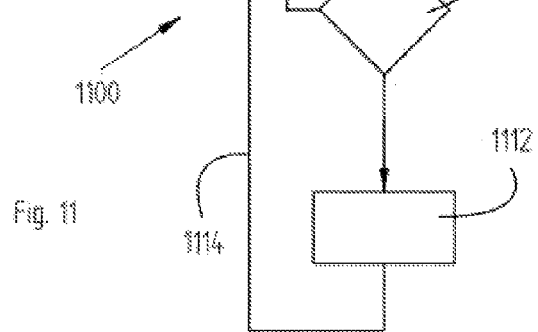
FIG. 11 shows a control algorithm for the sensor of FIG. 7 or FIG. 9.

FIG. 11 shows an algorithm of a control method 1100 according to the invention that can be used for a sensor 700 shown in FIGS. 7 and 8.

The control method 1100 comprises:
  an initialisation step 1102 during which the detection means 750 sends to the control unit 124 the reference value representing the light power that it receives in the absence of the part,
  a sending step 1104 during which the detection means 750 sends to the control unit 124 a value representing the light power that it receives, a computing step 1106 during which the control unit 124 computes the difference between the value thus received and the reference value, a test step 1108 during which the control unit 124 checks whether the difference thus computed is greater in absolute value than a predetermined difference, if the difference thus computed remains below the predetermined difference, a looping step 1110 during which the process loops onto the sending step 1104, if the difference thus computed is greater than the predetermined difference, a control step 1112 during which the control unit 124 demands an increase in the light power emitted by the illumination source 102, and a return step 1114 during which the process loops onto the sending step 1104.

Figure 9:
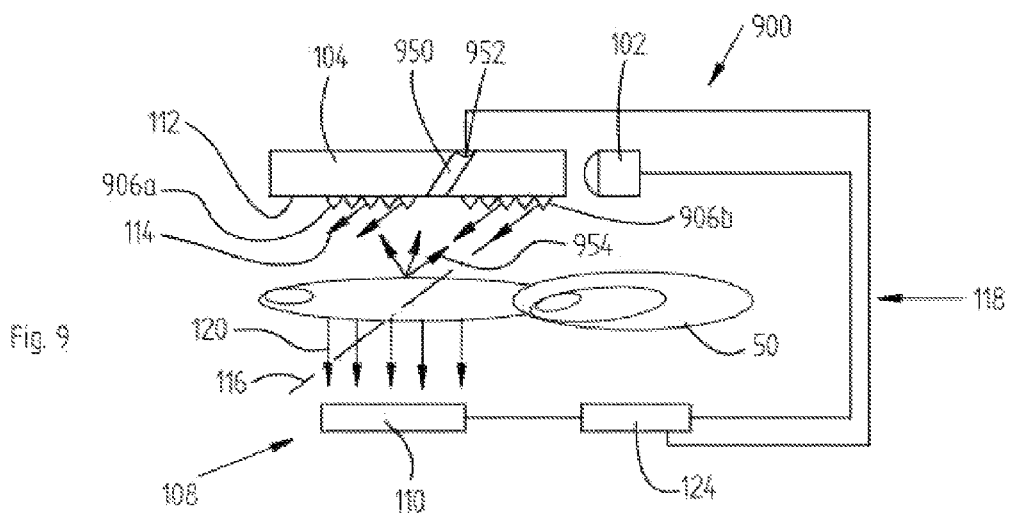
FIG. 9 shows a side view of a venous network sensor according to an eighth embodiment of the invention.
Figure 10:
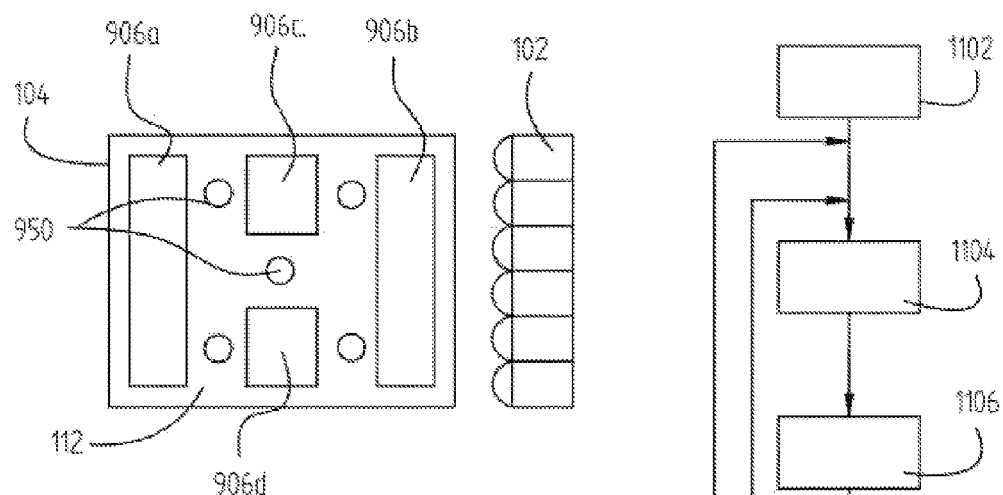
FIG. 10 shows a view from below of the venous network sensor of FIG. 9.

FIG. 9 and FIG. 10 show a sensor 900 also comprising means for controlling the illumination source 102 in order to control the illumination source 102 for power depending on whether the finger 50 is present or not in the passage 118.

The control means consist here of one or more detection means 952 and the control unit 124.

The detection means 952 are here disposed in the vicinity of the extraction zones 906*a-d*.

In the absence of the finger 50, the detection means 952 receive practically no infrared rays while, when the finger 50 is present, the detection means 952 then capture the infrared rays 952 backscattered by the finger 50 towards the waveguide 104.

Thus, according to the light power that they receive, the detection means 952 send a value representing this light power to the control unit 124 which, depending on this value, controls the illumination source 102 so as to increase or not the light power that it emits by virtue of appropriate means that it comprises.

To prevent the detection means 952 being disturbed by the infrared rays reflected by the skin of the finger 50, each is disposed at the bottom of a hole 950 produced in the waveguide 104, each of said holes 950 having an axis substantially parallel to the extraction direction 116 in order to protect the detection means 952 from the infrared rays directly reflected by the finger 50.

To prevent the detection means 952 being disturbed by the infrared rays passing through the waveguide 104, the surface of said holes 950 is covered with a material impermeable to infrared rays.

Another control method may consist of analysing the average contrast level of the image of the venous network captured and controlling the initial part of the illumination source 102 according to this average level.

In each above embodiment, the face 112 where the extraction zone 106 is disposed constitutes the extraction face 112 through which the infrared rays 114, 714*a*, 714*b* are extracted, and the image acquisition means 108 is disposed opposite the extraction face 112.

Figure 12:
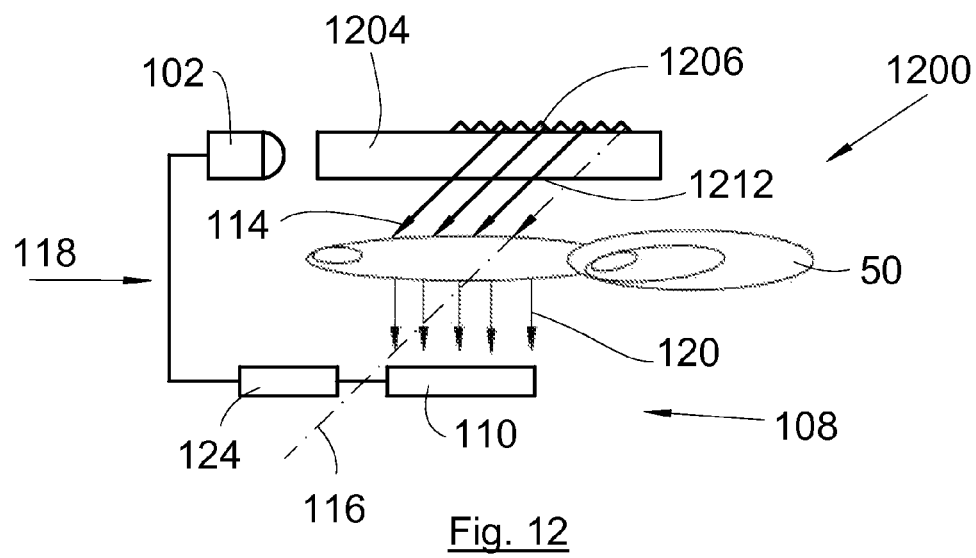
FIG. 12 shows a side view of a venous network sensor according to a ninth embodiment of the invention.

FIG. 12 shows a sensor 1200 according to a ninth embodiment of the invention, which comprises:

an infrared illumination source 102, a waveguide 1204 illuminated by the infrared illumination source 102 and having at least one extraction zone 1206 intended to extract the infrared rays 114 from the waveguide 1204 in at least one main extraction direction 116 through an extraction face 1212 of said waveguide 1204, an image acquisition means 108 disposed opposite said extraction face 1212 so as to define between them a passage 118 through the entrance of which said part 50 of the living body can enter, and comprising a sensitive element 110, the or each extraction zone 1206 being such that the or each main extraction direction 116 is oriented so as not to intercept said sensitive element 110.

Unlike the previous embodiments, the extraction face 1212 of the sensor 1200 is not the face that carries the extraction zone 1206, but the face opposite to the face that carries the extraction zone 1206.

The extraction zone 1206 may also be in the form of a patch that is optically coupled to the face opposite to the extraction face 1212 of the waveguide 1204 and comprises here prisms, more particularly microprisms that are used in reflection.

In this embodiment where the slope of each microprism is at 70° with respect to the normal to the extraction face 1212, the main extraction direction 116 has an angle of approximately 8° with the normal to the extraction face 1212. Such a positioning of the extraction zone makes it possible to obtain an angularly tight emission layer.

The surface under reflection in this embodiment is greater and the photon coupling efficiencies are better with lower leakage rates.

The layer generated undergoes overall an additional refraction that increases the elementary emission solid angle.

Naturally it is possible to apply the teaching of the above embodiments to the embodiment in FIG. 12. For example, it is possible to dispose the light source 102 at the opposite end to the entrance of the passage 118 (FIG. 2), disposing a reflective surface having an angle of inclination designed to bend the infrared rays transmitted and divert them towards the or each extraction zone 1206. For example, it is possible to provide an implementation similar to that of FIG. 3. It is also possible to fit a protective plate placed facing the face opposite to the extraction face 1212 and consisting of a material preventing the passage of the infrared rays but allowing the rays in the visible spectrum to pass. It is also possible to dispose a filtering plate between the extraction zone 1206 and the passage 118 and consisting of a material preventing the passage of rays in the visible spectrum but allowing infrared rays to pass. It is also possible to use control means designed to control the illumination source 102 for power.

Figure 13:
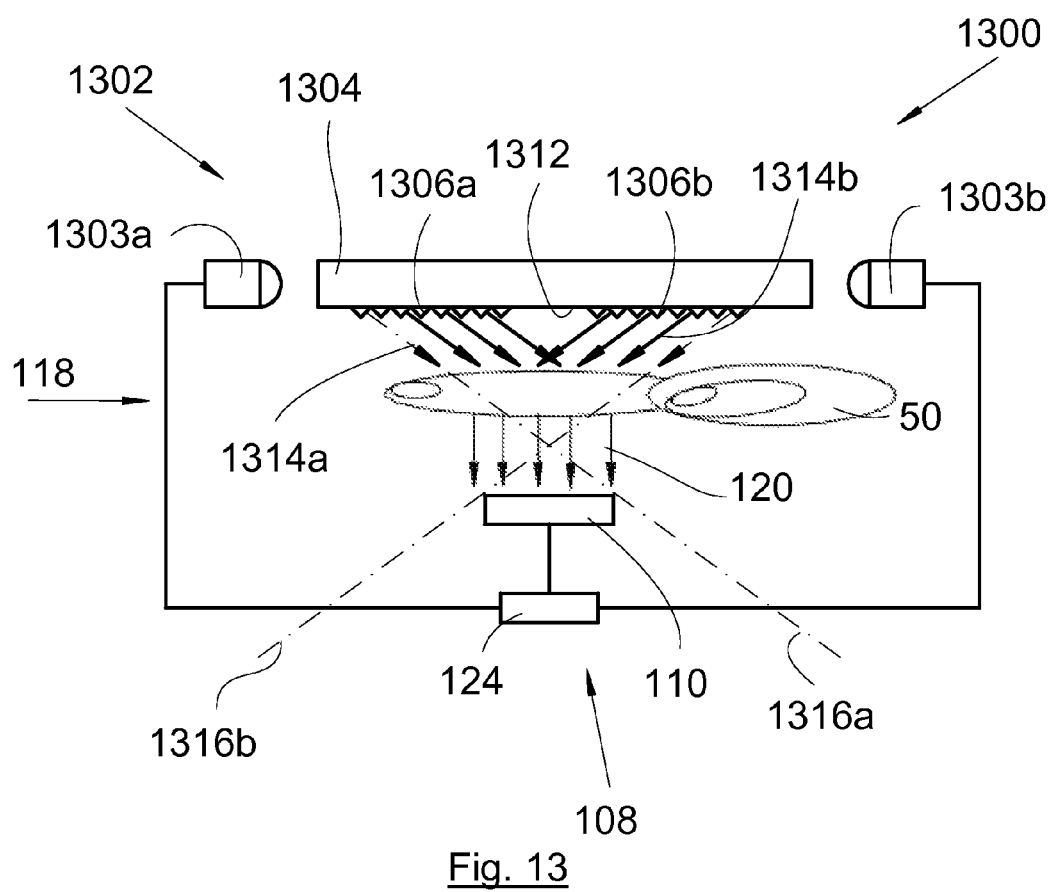
FIG. 13 shows a side view of a venous network sensor according to a tenth embodiment of the invention.

FIG. 13 shows a sensor 1300 according a tenth embodiment of the invention.

The sensor 1300 comprises:

an infrared illumination source 1302, and an image acquisition means 108.

The sensor 1300 also comprises a waveguide 1304 illuminated by said infrared illumination source 1302 and having a first extraction zone 1306*b* and a second extraction zone 1306*a*, each being intended to extract the infrared rays 1314*a* and 1314*b* from the waveguide 1304 through an extraction face 1312 of the waveguide 1304 in a main extraction direction respectively referenced 1316*a* and 1316*b*.

The image acquisition means 108 is disposed facing the extraction face 1312 so as to define between them a passage 118 through the entrance of which the part 50 of the living body can enter, and comprises a sensitive element 110.

Each extraction area 1306*a*, 1306*b* is such that each main extraction direction 1316*a*, 1316*b* is oriented so as not to intercept said sensitive element 110.

In the embodiment of the invention presented in FIG. 13, each extraction zone 1306*a*, 1306*b* is carried by the extraction face 1312.

The illumination source 1302 has a first illuminating element 1303*b* illuminating the edge of the waveguide 1304 disposed on the same side as the entrance of the passage 118, and a second illuminating element 1303a illuminating the edge of the waveguide 1304 disposed on the side opposite to the entrance of the passage 118. The illuminating elements 1303a and 1303b are for example of the diode array type.

Each extraction zone 1306a, 1306b here consists of microprisms.

The first extraction zone 1306b is disposed between the first illuminating element 1303b and the second extraction zone 1306a, and is designed to extract the infrared rays 1314b issuing from the first illuminating element 1303b.

The second extraction zone 1306a is disposed between the second illuminating element 1303a and the first extraction zone 1306b, and is designed to extract the infrared rays 1314a issuing from the second illuminating element 1303a.

The extraction zones 1306a and 1306b are such that the infrared rays 1314b extracted from the waveguide 1304 through the first extraction zone 1306b and the infrared rays 1314a extracted from the waveguide 1304 through the second extraction zone 1306a converge towards each other at the point in the passage 118 where the part 50 of the living body is liable to be positioned and upstream of the image acquisition means 108.

It is thus possible to balance the illumination of the part 50.

Naturally the present invention is not limited to the examples and embodiments described and depicted but is capable of numerous variants accessible to a person skilled in the art.

The invention claimed is:

1. Sensor (100, 200, 300, 400, 500, 600, 700, 900, 1200, 1300) for venous networks of a part (50) of a living body, comprising:
    an infrared illumination source (102,1302), and
    an image acquisition means (108),
    said sensor (100, 200, 300, 400, 500, 600, 700, 900, 1200, 1300) further comprising a waveguide (104, 204, 304, 404, 1204, 1304) illuminated by said infrared illumination source (102, 1302) and having at least one extraction zone (106, 450, 506, 906a-d, 1206, 1306a, 1306b) intended to extract the infrared rays (114, 714a, 714b, 1314a, 1314b) from said waveguide (104, 204, 304, 404, 1204, 1304) through an extraction face (112, 1212, 1312) of the waveguide (104, 204, 304, 404, 1204, 1304) in at least one main extraction direction (116, 452, 550, 1316, 1316b),
    wherein said image acquisition means (108) is disposed facing said extraction face (112, 1212, 1312) so as to define between them a passage (118) through the entrance of which said part (50) of the living body can enter, and comprising a sensitive element (110), and
    wherein the or each extraction zone (106, 450, 506, 906a-d, 1206, 1306a, 1306b) is such that the or each main extraction direction (116, 452, 550, 1316a, 1316b) is oriented so as not to intercept said sensitive element (110).

2. Sensor (1200) according to claim 1, wherein said or each extraction zone (1206) is carried by the face opposite to the extraction face (1212).

3. Sensor (100, 200, 300, 400, 500, 600, 700, 900, 1300) according to claim 1, wherein said or each extraction zone (106, 506, 906a-d, 1306a, 1306b) is carried by the extraction face (112, 1312).

4. Sensor (100, 200, 300, 400, 500, 600, 700, 900) according to claim 1, wherein at least one of said extraction zones (450) consists of an inclined facet (450) produced in said extraction face (112).

5. Sensor (400) according to claim 4, wherein the inclined facet (450) is upstream of the microprisms in the direction of progression of the infrared rays (122) in the waveguide (404).

6. Sensor (100, 200, 300, 400, 500, 600, 700, 900, 1200, 1300) according to claim 1, wherein at least one of said extraction zones (106, 506, 906a-d, 1206, 1306a, 1306b) consists of microprisms.

7. Sensor (200) according to claim 1, wherein the light source (102) is disposed opposite the entrance of the passage (118), wherein the sensor (200) comprises a collimation means (252) disposed between the illumination source (102) and the waveguide (204) and designed to collimate close to infinity the infrared rays issuing from the illumination source (102), and wherein the waveguide (204) has, on the path of the infrared rays (122) thus collimated, a reflective surface (250) having an angle of inclination designed to bend the infrared rays (122) transmitted and divert them to the or each extraction zone (106).

8. Sensor (300) according to claim 1, wherein the light source (102) is disposed opposite the entrance of the passage (118), wherein the sensor (300) comprises a focusing means (352) disposed between the illumination source (102) and the waveguide (304) and designed to focus the infrared rays issuing from the illumination source (102) towards a focusing point (354), and wherein the waveguide (304) has, on the path of the infrared rays (122) thus focused, a reflective surface (350) disposed at a distance from the distance from the focusing point (354) and designed to reflect the infrared rays (122) and cause diversion thereof towards the extraction zone (106).

9. Sensor (1300) according to claim 1, wherein said waveguide (1304) has a first extraction zone (1306b) and a second extraction zone (1306a), wherein said infrared illumination source (1302) has a first illuminating element (1303b) illuminating the edge of the waveguide (1304) disposed on the passage entrance side (118), and a second illuminating element (1303a) illuminating the edge of the waveguide (1304) disposed on the side opposite to the passage entrance (118), wherein the first extraction zone (1306b) is disposed between the first illuminating element (1303b) and the second extraction zone (1306a) and is designed to extract the infrared rays (1314b) issuing from the first illuminating element (1303b), wherein the second extraction zone (1306a) is disposed between the second illuminating element (1303a) and the first extraction zone, and is designed to extract the infrared rays (1314a) issuing from the second illuminating element (1303a), and wherein the extraction zones (1306a, 1306b) are such that the infrared rays (1314b) extracted by the first extraction zone (1306b) and the infrared rays (1314a) extracted by the second extraction zone (1306a) converge towards each other at the point in the passage (118) where the part is liable to be positioned (50).

10. Sensor (600) according to claim 1, wherein it comprises a protective plate (650) placed opposite the face opposite to the extraction face (112) and consisting of a material preventing the passage of infrared rays but allowing rays in the visible spectrum to pass.

11. Sensor (600) according to claim 1, wherein it comprises a filtering plate (652) placed between the extraction zone (106) and the passage (118) and consisting of the material preventing the passage of rays in the visible spectrum but allowing infrared rays to pass.

12. Sensor (700, 900) according to claim 1, wherein it comprises control means (750, 952, 124) designed to control the illumination source (102).

13. Sensor (700, 900) according to claim 12, wherein the control means consist of a control unit (124) designed to control the illumination source (102) and at least one detection means (750, 952) designed to send to said control unit (124) a value representing the illumination power that it receives, the control unit (124) comprising means for controlling the illumination source (102) according to said value.

14. Method (1100) for controlling a sensor (700) according to claim 13, said method (1100) comprising:
- an initialisation step (1102), during which the detection means (750) sends to the control unit (124) the reference value representing the light power that it receives in the absence of the part,
- a sending step (1104), during which the detection means (750) sends to the control unit (124) a value representing the light power that it receives,
- a calculation step (1106) during which the control unit (124) calculates the difference between the value thus received and the reference value,
- a test step (1108), during which the control unit (124) checks whether the difference thus calculated is greater, in absolute value, than a predetermined difference,
- if the difference thus calculated remains less than the predetermined difference, a looping step (1100) during which the process loops back onto the sending step (1104),
- if the difference thus calculated is greater than the predetermined difference, a control step (1112) during which the control unit (124) demands an increase in the light power emitted by the illumination source (102), and
- a return step (1114) during which the process loops back onto the sending step (1104).

15. Sensor (700) according to claim 12, wherein the or each detection means (750) is placed in the vicinity of the sensitive element (110).

16. Sensor (900) according to claim 12, wherein the or each detection means (952) is disposed in the vicinity of the extraction zone or zones (906a-d).

17. Sensor (900) according to claim 16, wherein the or each detection means (952) is disposed at the bottom of a hole produced in the waveguide (104), each of said holes (950) having an axis substantially parallel to the extraction direction (116).

18. Sensor (900) according to claim 17, wherein the surface of the or each hole (950) is covered with a material impermeable to infrared rays.

* * * * *